(12) United States Patent  (10) Patent No.: US 8,226,593 B2
Graham et al.  (45) Date of Patent: Jul. 24, 2012

(54) PYLORIC VALVE

(75) Inventors: Marc Graham, Somerville, MA (US); Buket Grau, Arlington, MA (US)

(73) Assignee: E2 LLC, Morris Plains, NJ (US)

( * ) Notice: Subject to any disclaimer, the term of this patent is extended or adjusted under 35 U.S.C. 154(b) by 497 days.

(21) Appl. No.: 12/420,219

(22) Filed: Apr. 8, 2009

(65) Prior Publication Data

US 2009/0259240 A1   Oct. 15, 2009

Related U.S. Application Data

(60) Provisional application No. 61/123,472, filed on Apr. 9, 2008.

(51) Int. Cl.
*A61M 5/00* (2006.01)
*A61F 2/04* (2006.01)

(52) U.S. Cl. .............. 604/9; 604/8; 623/23.68

(58) Field of Classification Search ........ 604/8–10; 128/898; 606/108; 623/23.64–23.68
See application file for complete search history.

(56) References Cited

U.S. PATENT DOCUMENTS

| | | |
|---|---|---|
| 4,315,509 A | 2/1982 | Smit |
| 4,501,264 A | 2/1985 | Rockey |
| 5,306,300 A | 4/1994 | Berry |
| 5,401,241 A | 3/1995 | Delany |
| 5,820,584 A | 10/1998 | Crabb |
| 5,993,473 A | 11/1999 | Chan et al. |
| 6,271,278 B1 | 8/2001 | Park et al. |
| 6,454,785 B2 | 9/2002 | De Hoyos Garza |
| 6,540,789 B1 | 4/2003 | Silverman et al. |
| 6,544,291 B2 | 4/2003 | Taylor |
| 6,558,400 B2 | 5/2003 | Deem et al. |
| 6,675,809 B2 | 1/2004 | Stack et al. |
| 6,740,121 B2 | 5/2004 | Geitz |
| 6,755,869 B2 | 6/2004 | Geitz |
| 6,764,518 B2 | 7/2004 | Godin |
| 6,802,868 B2 | 10/2004 | Silverman et al. |
| 6,845,776 B2 | 1/2005 | Stack et al. |
| 6,946,002 B2 | 9/2005 | Geitz |
| 6,981,978 B2 | 1/2006 | Gannoe |
| 6,994,095 B2 | 2/2006 | Burnett |
| 7,025,791 B2 | 4/2006 | Levine et al. |
| 7,033,384 B2 | 4/2006 | Gannie et al. |
| 7,037,343 B2 | 5/2006 | Imran |

(Continued)

FOREIGN PATENT DOCUMENTS

WO   WO 03/086247   10/2003

(Continued)

*Primary Examiner* — Tatyana Zalukaeva
*Assistant Examiner* — Philip R Wiest
(74) *Attorney, Agent, or Firm* — John T. Raffle

(57) ABSTRACT

A pyloric valve for regulating the flow of fluids in the pyloric region a patient's gastrointestinal tract is disclosed herein. In one embodiment, a pyloric valve includes a plurality of axially connected blocking members located along a longitudinal axis of the valve in a proximal to distal direction. Each blocking member of the valve preferably includes at least one blocking portion defining at least one entryway adapted to receive fluids such as chyme therethrough. The at least one entryway of each blocking member is preferably not aligned with the at least one entryway of each blocking member adjacent thereto along the longitudinal axis. The non-alignment of the at least one entryways of the blocking members preferably creates a non-linear path for fluids such as chyme to travel through the pyloric region of the patient.

12 Claims, 8 Drawing Sheets

U.S. PATENT DOCUMENTS

| | | |
|---|---|---|
| 7,037,344 B2 | 5/2006 | Kagan et al. |
| 7,044,979 B2 | 5/2006 | Silverman et al. |
| 7,090,699 B2 | 8/2006 | Geitz |
| 7,097,665 B2 | 8/2006 | Stack et al. |
| 7,111,627 B2 | 9/2006 | Stack et al. |
| 7,118,600 B2 | 10/2006 | Dua et al. |
| 7,121,283 B2 | 10/2006 | Stack et al. |
| 7,122,058 B2 | 10/2006 | Levine et al. |
| 7,152,607 B2 | 12/2006 | Stack et al. |
| 7,214,233 B2 | 5/2007 | Gannoe et al. |
| 7,220,284 B2 | 5/2007 | Kagan et al. |
| 7,267,694 B2 | 9/2007 | Levine et al. |
| 2003/0040808 A1 | 2/2003 | Stack et al. |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0117031 A1 | 6/2004 | Stack et al. |
| 2004/0122526 A1 | 6/2004 | Imran |
| 2004/0148034 A1 | 7/2004 | Kagan et al. |
| 2004/0172141 A1 | 9/2004 | Stack et al. |
| 2004/0172142 A1 | 9/2004 | Stack et al. |
| 2004/0204768 A1 | 10/2004 | Geitz |
| 2004/0220682 A1 | 11/2004 | Levine et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0080491 A1 | 4/2005 | Levine et al. |
| 2005/0085923 A1 | 4/2005 | Levine et al. |
| 2005/0096750 A1 | 5/2005 | Kagan et al. |
| 2005/0125020 A1 | 6/2005 | Meade et al. |
| 2005/0177181 A1 | 8/2005 | Kagan et al. |
| 2005/0192614 A1 | 9/2005 | Binmoeller |
| 2005/0273060 A1* | 12/2005 | Levy et al. .................. 604/192 |
| 2006/0009858 A1 | 1/2006 | Levine et al. |
| 2006/0064120 A1 | 3/2006 | Levine et al. |
| 2006/0129237 A1 | 6/2006 | Imran |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0265082 A1 | 11/2006 | Meade et al. |
| 2006/0287734 A1 | 12/2006 | Stack et al. |
| 2007/0005147 A1 | 1/2007 | Levine et al. |
| 2007/0010865 A1 | 1/2007 | Dann et al. |
| 2007/0032879 A1 | 2/2007 | Levine et al. |
| 2007/0083224 A1 | 4/2007 | Hively |
| 2007/0135831 A1 | 6/2007 | Burnett |
| 2007/0149994 A1 | 6/2007 | Sosnowski et al. |
| 2007/0156248 A1 | 7/2007 | Marco et al. |
| 2007/0178160 A1 | 8/2007 | Burnett |
| 2008/0109087 A1* | 5/2008 | Durgin .................. 623/23.65 |

FOREIGN PATENT DOCUMENTS

| | | |
|---|---|---|
| WO | WO 2006/127593 | 11/2006 |
| WO | WO 2007/030829 | 3/2007 |
| WO | WO 2007/053556 | 5/2007 |

* cited by examiner

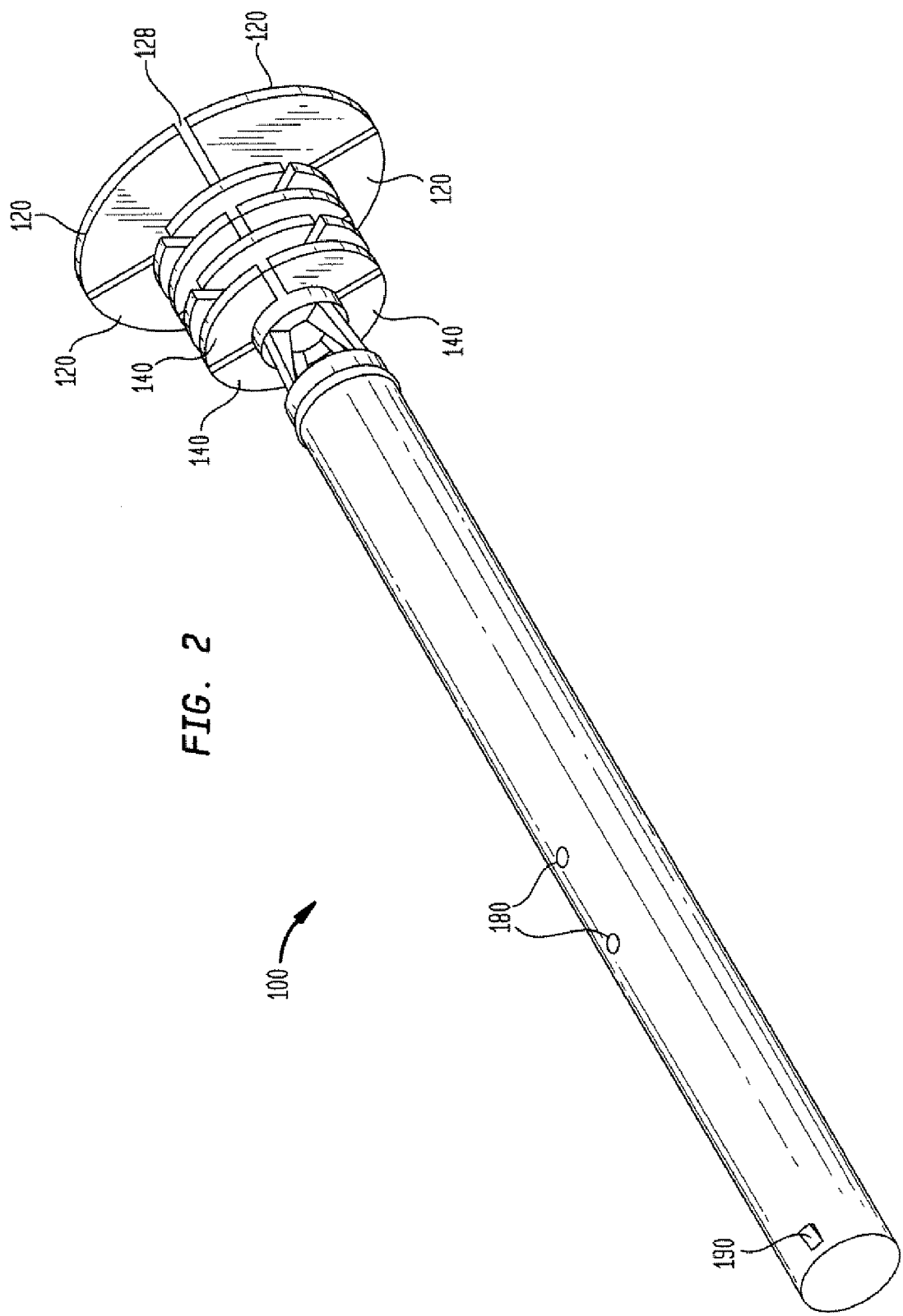

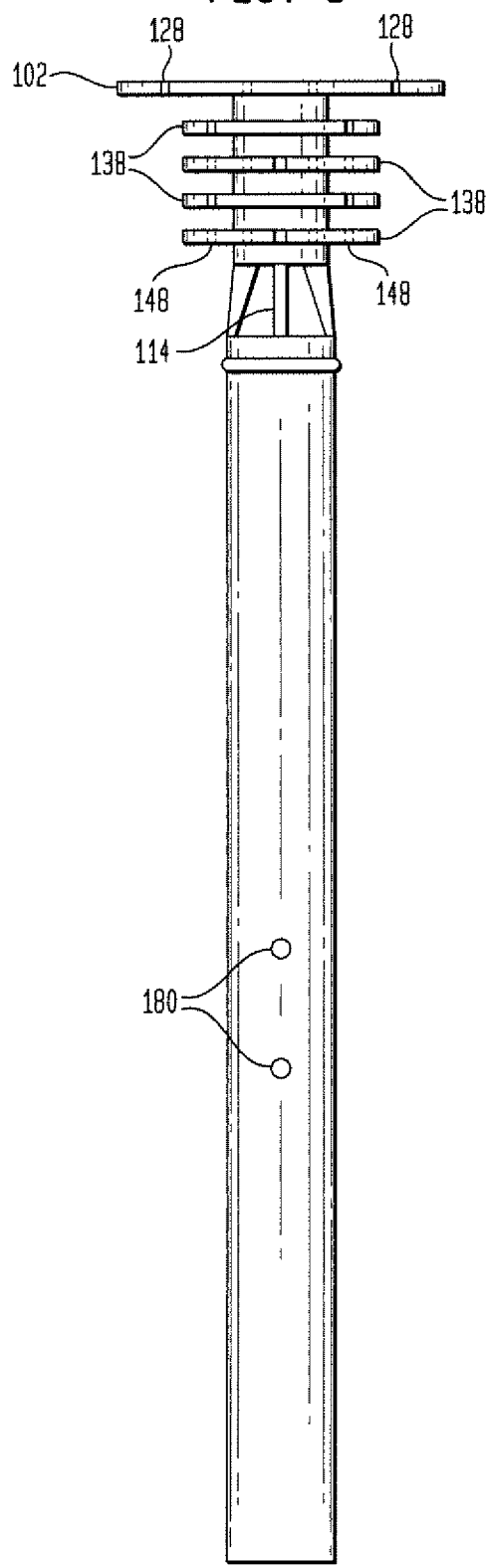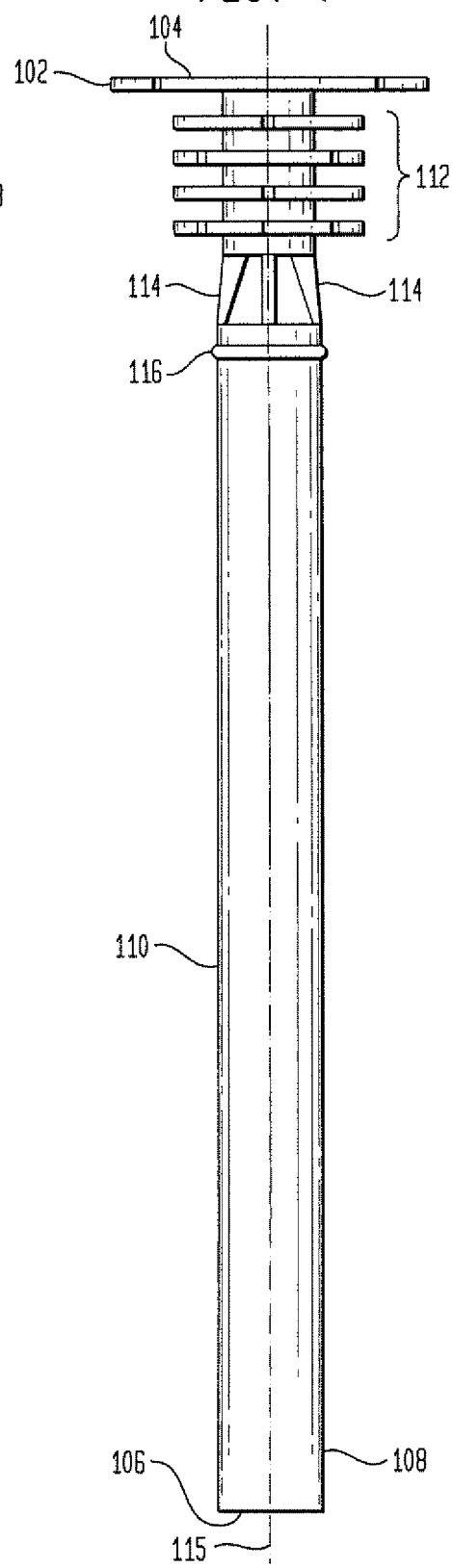

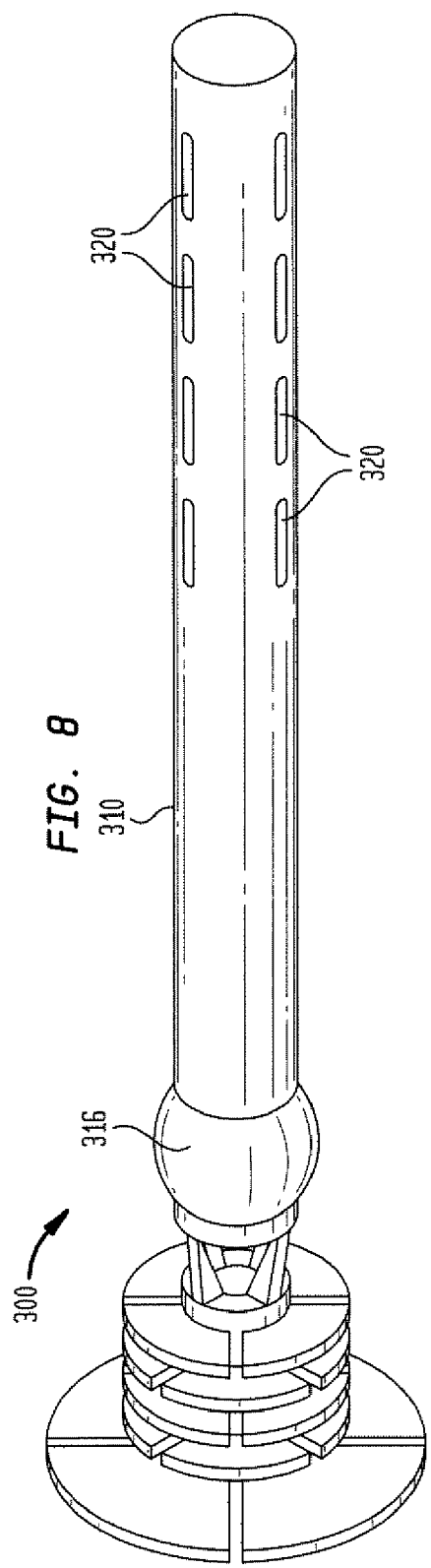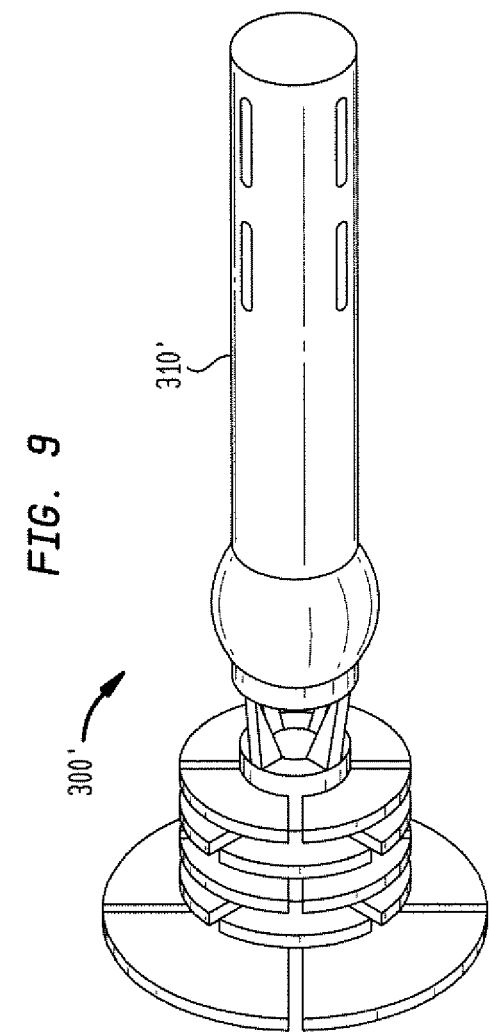

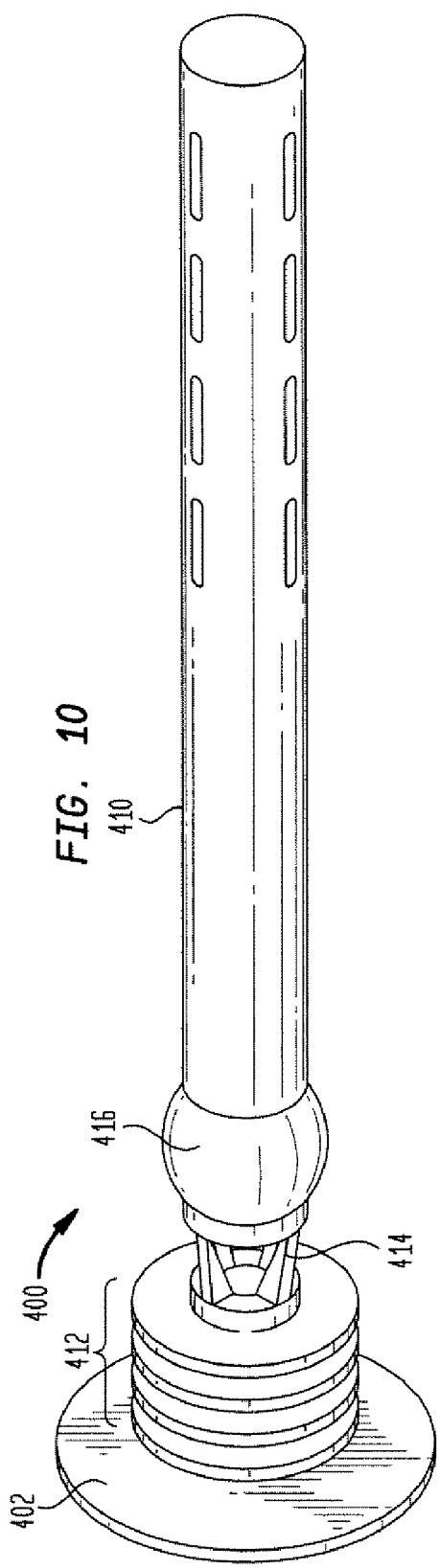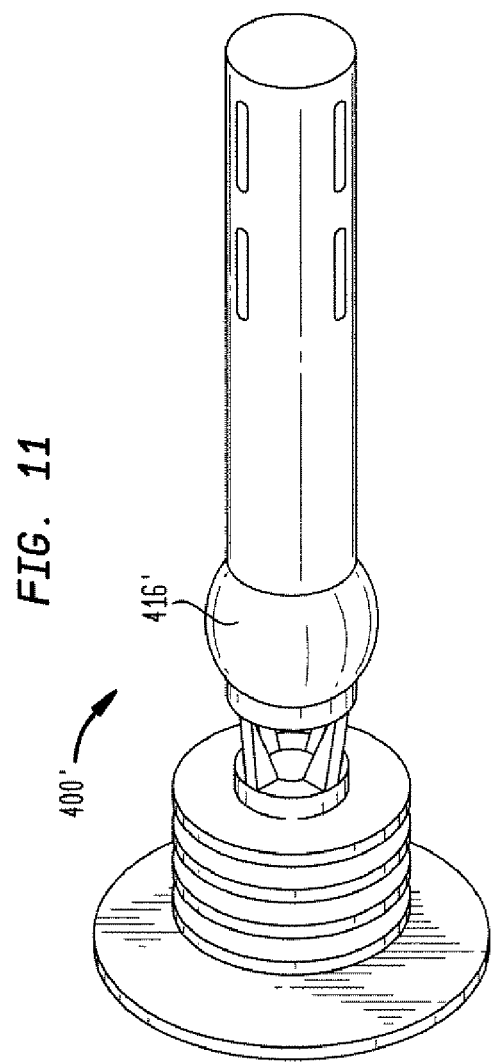

PYLORIC VALVE

CROSS-REFERENCE TO RELATED APPLICATIONS

This application claims the benefit of the filing dates of U.S. Provisional Patent Application No. 61/123,472 filed Apr. 9, 2008, entitled PYLORIC VALVE, the disclosure of which is hereby incorporated herein by reference.

FIELD OF THE TECHNOLOGY

The present invention relates to a device implanted in the gastrointestinal tract to aid in controlling obesity, and more particularly relates to a pyloric valve implanted in the pyloric region of the stomach to control the flow of chyme through the stomach.

BACKGROUND OF THE INVENTION

Obesity is a condition in which the natural energy reserve, stored in the fatty tissue of humans and other mammals, is increased to a point where it is associated with certain adverse health conditions. Although obesity is an individual clinical condition, it is increasingly viewed as a serious and growing public health problem. Excessive body weight has been shown to predispose to various diseases, particularly cardiovascular diseases, diabetes mellitus type 2, sleep apnea and osteoarthritis.

The main treatment for obesity is to reduce body fat by eating fewer calories and increasing exercise. A beneficial side effect of exercise is to increase muscle, tendon, and ligament strength, which helps to prevent injury from accidents and vigorous activity. Diet and exercise programs produce an average weight loss of approximately 8% of total body mass (excluding program drop-outs). Not all dieters are satisfied with these results, but a loss of as little as 5% of body mass can create large health benefits. Much more difficult than reducing body fat is keeping it off. Eighty to ninety-five percent of those who lose 10% or more of their body mass by dieting regain all that weight back within two to five years.

The body has systems that maintain its homeostasis at certain set points, including body weight. Therefore, keeping weight off generally requires making exercise and healthy eating a permanent part of a person's lifestyle. Certain nutrients or chemicals, such as phenylalanine, are natural appetite suppressants which allow resetting of the body's set point for body weight. However, diet, and exercise and/or appetite suppressants may not result in sufficient weight loss for patients with serious medical conditions.

An alternative mechanism for hunger suppression is to decrease the rate of gastric emptying without the use of ingesting chemicals. In effect, obesity can be controlled by implanting a device in the gastrointestinal tract that may regulate satiety. It should be understood that the effects of regulating satiety may vary between individuals.

Partially undigested food in the gastrointestinal track is generally referred to as chyme. A need exists for a device that is structured to inhibit the rate that chyme passes through the gastrointestinal track while allowing natural peristaltic action to occur.

Satiety receptors are generally located all along the stomach. If chyme remains in the stomach for a longer period of time than it naturally would before flowing into the small intestine, then the satiety receptors have a greater chance of being activated to signal the sensation of being satiated. Thus, a device implanted in the stomach and/or small intestine may enhance the ability of an overweight or obese patient to feel satiated so that the patient does not overeat, and in fact eat less than normal.

SUMMARY OF THE INVENTION

A first aspect of the present invention is a pyloric valve. In accordance with one embodiment of this first aspect, the pyloric valve includes a plurality of axially connected blocking members located along a longitudinal axis of the valve in a proximal to distal direction. Preferably, each blocking member defines at least one entryway adapted to receive chyme therethrough, wherein the at least one entryway defined by each blocking member is not aligned along the longitudinal axis with the at least one entryway defined by each blocking member adjacent thereto.

A second aspect of the present invention is a pyloric valve. In accordance with one embodiment of this second aspect, the pyloric valve has a proximal section including a plurality of axially connected blocking members located along a longitudinal axis of the valve in a proximal to distal direction. Preferably, each blocking member defines at least one entryway adapted to receive chyme therethrough. Preferably, the at least one entryway defined by a first blocking member is not aligned with the at least one entryway defined by a second blocking member located adjacent to the first blocking member in the distal direction along the longitudinal axis such that chyme passing through the at least one entryway defined by the first blocking member cannot travel in a linear path through the at least one entryway defined by the second blocking member. The pyloric valve preferably further includes a distal section connected to the proximal section distally along the longitudinal axis, the distal section including an elongate sleeve adapted for the passage of the chyme therein.

A third aspect of the present invention is a pyloric valve. In accordance with one embodiment of this third aspect, the pyloric valve has an inlet formed at a proximal end of the pyloric valve. Preferably, the inlet has at least one entryway adapted to receive chyme therethrough. Preferably, the pyloric valve further includes at least one blocking member located distal to the entryway of the inlet, the blocking member adapted to receive chyme having flowed through the at least one entryway of the inlet thereon. Preferably, the at least one blocking member has at least one entryway misaligned with the at least one entryway of the inlet, wherein the chyme passing through the at least one entryway of the inlet cannot travel in a linear path through the at least one entryway of the blocking member. Preferably, the pyloric valve further includes an elongate sleeve located distal to the at least one blocking member, the elongate sleeve adapted for the passage of chyme therein.

In accordance with one embodiment of this third aspect of the present invention, the inlet includes at least one blocking portion having a first side surface, a second side surface, and a proximal surface, wherein the proximal surface is adapted to receive chyme thereon.

In accordance with another embodiment of this third aspect of the present invention, the at least one entryway is formed between the first side surface and the second side surface of the at least one blocking portion. Preferably, the at least one entryway is approximately 1-2 mm in width.

In accordance with yet another embodiment of this third aspect of the present invention, an entryway is formed between adjacent first and second side surfaces of adjacent blocking portions. Preferably, the at least one entryway is approximately 1-2 mm in width.

In accordance with still yet another embodiment of this third aspect of the present invention, the at least one blocking member includes a first side surface, a second side surface, and a proximal surface, wherein the proximal surface is adapted to receive the chyme thereon.

In accordance with still yet another embodiment of this third aspect of the present invention, the pyloric valve of the present invention further includes a plurality of blocking members distal to the inlet, wherein each successive blocking member is located distal to the blocking member that precedes it. Preferably, the plurality of blocking members each include a first side surface, a second side surface, and a proximal surface, wherein the proximal surface is adapted to receive the chyme thereon.

In accordance with still yet another embodiment of this third aspect of the present invention, the inlet includes a plurality of entryways.

In accordance with still yet another embodiment of this third aspect of the present invention, the pyloric valve of the present invention further includes pyloric columns connecting a distal end of the at least blocking member and a proximal end of the sleeve. Preferably, the sleeve includes at least one aperture therethrough, the at least one aperture adapted to receive fluid such as bile or other gastric secretions therein. Preferably, the sleeve further includes a radiopaque marker located on a surface of the sleeve or embedded throughout the device.

A fourth aspect of the present invention includes a method of regulating the flow of chyme through a stomach of a patient. Preferably, the steps of the method include implanting a pyloric valve into the pyloric region between a stomach and small intestines of the patient. Preferably, the pyloric valve includes an inlet formed at a proximal end of the pyloric valve, the inlet having at least one entryway adapted to receive chyme therethrough. Preferably, the pyloric valve further includes at least one blocking member located distal to the entryway of the inlet, the blocking member adapted to receive chyme having flowed through and/or around the at least one entryway of the inlet thereon. Preferably, the at least one blocking member has at least one entryway misaligned with the at least one entryway of the inlet, wherein the chyme passing through and/or around the at least one entryway of the inlet cannot travel in a linear path through the at least one entryway of the blocking member. Preferably, the pyloric valve further includes an elongate sleeve located distal to the at least one blocking member, the elongate sleeve adapted for the passage of chyme therein. Preferably the pyloric valve further includes a plurality of pyloric columns connecting a distal end of the at least blocking member and a proximal end of the sleeve, the plurality of pyloric columns being compliant such that the natural peristaltic action of the pyloric sphincter is not inhibited by the plurality of the pyloric columns. Preferably, the pyloric valve is implanted such that the inlet is located adjacent the pyloric antrum of the stomach, the at least one blocking member is located proximal to the pyloric sphincter, the plurality of the pyloric columns are located adjacent the pyloric sphincter, and the sleeve is located distal to the pyloric sphincter, the sleeve beginning in the duodenum and terminating in the small intestines.

A fifth aspect of the present invention includes a method of regulating the flow of chyme through a stomach of a patient. Preferably, the steps of the method include placing an endoscopic delivery tool into a stomach of a patient; passing a pyloric valve through the endoscopic delivery tool; and implanting the pyloric valve in the pyloric region of the stomach. Preferably, the pyloric valve includes an inlet having at least one entryway formed therein; at least one blocking member located distal to the entryway of the inlet; a duodenal ring adapted to maintain the position of a portion of the valve adjacent to the pyloric sphincter; and a sleeve, wherein at least a portion of the sleeve is located distal to the duodenal ring such that chyme passing through the stomach is allowed to come in contact with the inlet and blocking members before flowing through the sleeve.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 2 is a perspective view of a pyloric valve of the present invention.

FIG. 3 is a side elevational view of the pyloric valve of FIG. 2 showing the presence of a plurality of bile holes along a sleeve of the pyloric valve.

FIG. 4 is a an alternative side elevational view of the pyloric valve of FIG. 2, wherein the pyloric valve is shown rotated approximately 90 degrees from the orientation it is shown in FIG. 3.

FIG. 8 is a view of another embodiment of a pyloric valve in accordance with the present invention shown having a duodenal ring structured to aid in anchoring the pyloric valve in the duodenum.

FIG. 9 is a view of another embodiment of a pyloric valve in accordance with the present invention having a shorter sleeve than the pyloric valve shown in FIG. 8.

FIG. 10 is another embodiment of a pyloric valve in accordance with the present invention having a plurality of blocking members with no entryways.

FIG. 11 is a view of another embodiment of a pyloric valve in accordance with the present invention having a shorter sleeve than the pyloric valve shown in FIG. 10.

DETAILED DESCRIPTION

As used herein, when referring to parts of the body, the term "proximal" means closer to the heart and the term "distal" means more distant from the heart. The term "inferior" means lower or bottom and the term "superior" means upper or top. The term "anterior" means towards the front part of the body or the face and the term "posterior" means towards the back of the body. The term "medial" means toward the midline of the body and the term "lateral" means away from the midline of the body.

Figure 1:
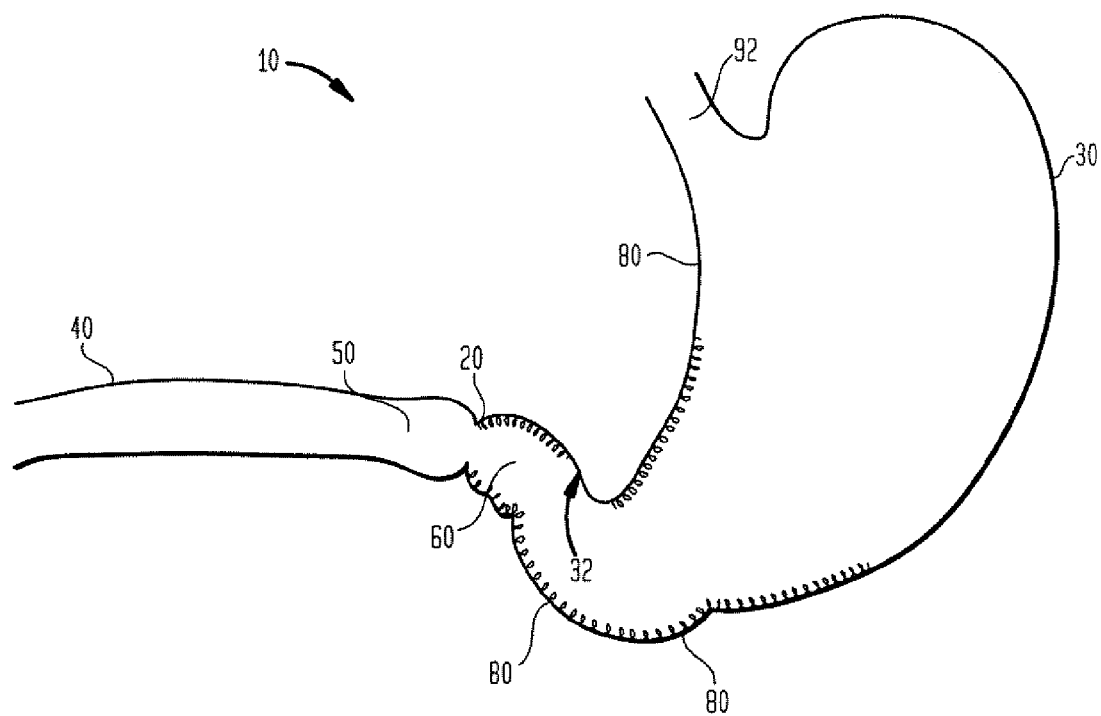
FIG. 1 is a view of a portion of a normal gastrointestinal tract of a human.

Referring to the drawings, wherein like reference numerals refer to like elements, there is shown in FIG. 1 an example of a portion of a gastrointestinal tract 10 of a human body. Two smooth muscle valves, or sphincters, contain the contents of the stomach within the stomach upon ingestion. They are the esophageal sphincter (not shown) found in the cardiac region above the antrum cardiacum, and the pyloric sphincter 20 shown dividing the stomach 30 from the small intestine 40. Pyloric sphincter 20 is a strong ring of smooth muscle at the end of the pyloric canal functioning to help regulate the passage of chyme from stomach 30 to the duodenum 50. Partially undigested food in the gastrointestinal track is generally referred to as chyme. Preferably, pyloric sphincter 20 controls the flow of chyme therethrough by way of natural peristaltic action causing sphincter 20 to alternate between a relaxed state and a contracted state. As shown in FIG. 1, the pyloric antrum 60 is located between stomach 30 and pyloric sphincter 20 or it can be said that pyloric antrum 60 is located proximally to pyloric sphincter 20. Therefore, duodenum 50 is located distally to pyloric sphincter 20.

Humans generally have satiety receptors 80 located all along the inside lining of stomach tissue as shown in FIG. 1. If chyme remains in the region of the stomach before flowing into the small intestine, then satiety receptors 80 have a greater chance of being activated, which enhances the ability of an overweight or obese patient to feel satiated such that they may have a reduction in their desire to eat.

Referring to FIGS. 2-5, an embodiment of the pyloric valve of the present invention is designated generally by reference numeral 100. Preferably, pyloric valve 100 is made of silicone or any other biocompatible polymeric material. Pyloric valve 100 is preferably a polymeric structure that is compliant and generally bendable while having sufficient strength properties to prevent unintended deformation thereof. Some portions of pyloric valve 100 may be thicker for enhanced strength properties. Preferably, if a portion of pyloric valve 10 is bent or twisted, the polymeric structure of the device allows it to change back to an initial shape or configuration.

Pyloric valve 100 is structured to inhibit the rate that chyme passes through gastrointestinal track 10 thereby reducing the rate of gastric emptying thereby enhancing the ability of chyme to activate satiety receptors 80 and in effect enhance satiety in a patient. Pyloric valve 100 is also structured to inhibit malabsorption, which is generally referred to as an abnormality where increased absorption of food occurs along the gastrointestinal tract.

Pyloric valve 100 may be delivered into stomach 30 of gastrointestinal track 10 through one of the methods disclosed in U.S. Provisional Patent Application No. 61/206,048 incorporated by reference herein in its entirety. Generally, an endoscope is placed through a patient's mouth and into the esophagus of a patient and through to the patient's stomach 30. Preferably, pyloric valve 100 is configured to have a lesser or collapsed diameter while contained within an endoscope and may be expanded to conform around a portion of inner surface 32 of adjacent stomach tissue after having been implanted in stomach 30. The compliant nature of pyloric valve 100 allows at least a portion of valve 100 to be collapsed and later opened or expanded into its initial configuration. Valve 10 may be made of shape memory material to expand back into an initial uncollapsed configuration.

If pyloric valve 100 is delivered to the pyloric region of stomach 30 in a collapsed state or position, valve 100 is preferably first expanded before the endoscope or endoscopic delivery tool is removed. Additional instruments (not shown) may be delivered to the region of stomach 30 in which pyloric valve 100 is implanted and used to expand and/or deliver the first blocking member or inlet 102 of valve 100. Preferably, inlet 102 is the first part of valve 100 chyme comes in contact with while traveling through gastrointestinal tract 10 and preferably has the largest diameter of all features included in pyloric valve 100.

Before the endoscope is removed from inside stomach 30 of a patient, inlet 102 is first placed in a preferable position in a pyloric region located just proximally of pyloric antrum 60 and a distal portion of valve 100 is located in at least the duodenum 50 and preferably is located in the small intestines 40. Inlet 102 may be set in the general location of the pyloric antrum 60 or even distal of pyloric antrum 60. While inlet 102 of valve may be set in a plurality of positions in the pyloric region, inlet 102 is preferably placed proximally of pyloric sphincter 20.

Pyloric valve 100 preferably includes a proximal end 104 and a distal end 106. As shown in FIGS. 3 and 4, located between proximal end 104 and distal end 106 of valve 100 from a proximal to distal direction are a plurality of axially connected blocking members or flanges preferably including an inlet 102 and blocking members 112, pyloric columns 114, duodenal ring 116, and sleeve 110. Inlet 102 is generally located at the proximal end 104 of valve 100 while a terminal end or portion 108 of sleeve 110 is generally located at the distal end 106 of valve 100.

Preferably, pyloric valve 100 includes a plurality of axially connected blocking members 112 located along a longitudinal axis 115 of the valve in a proximal to distal direction. Preferably, each blocking member 112 defines at least one entryway 148 adapted to receive chyme therethrough, wherein the at least one entryway 148 defined by each blocking member 112 is not aligned along longitudinal axis 115 with an at least one entryway 148 defined by each blocking member 112 located adjacent thereto.

During use, inlet 102 is the portion of pyloric valve 100 with the largest diameter such that the most amount of chyme may come in contact with the proximal end 104 of valve 100. First blocking member or inlet 102 preferably includes a first row of spaced apart flanges or blocking portions 120. First blocking member 102 is generally disc shaped having a plurality of entryways 128 forming the flange or blocking portions 120. Flanges 120 having a thickness measured from a proximal to distal end thereof of approximately 1 mm to 10 mm. Flanges 120 may be bent by a surgeon during positioning in stomach 20 to aid in the insertion thereof or may bend or flex due to contact with surrounding stomach tissue as natural peristaltic action of the stomach occurs.

Preferably, first blocking member 102 includes four blocking portions or flanges 120, but preferably includes at least one flange 120. In an embodiment wherein first blocking member 102 includes only one flange 120 there is no entryway 128 in first blocking member 102. Each flange 120 preferably has a proximal surface 122 adapted to receive chyme thereon. Each flange 120 preferably further includes a first side surface 124 and a second side surface 126 representing the thickness of each flange 120 as mentioned above.

Figure 5:
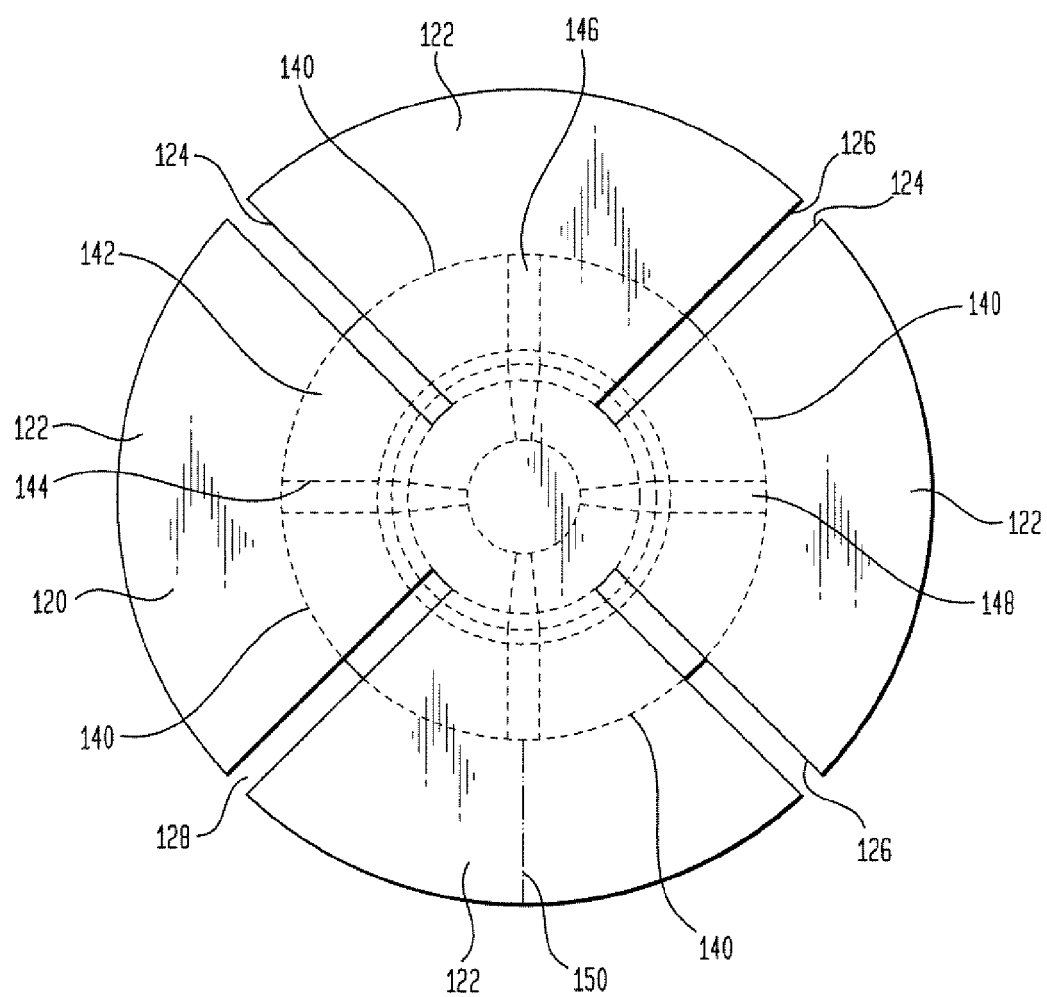
FIG. 5 is a top plan view of the pyloric valve of FIG. 2, showing a first blocking member or inlet of the pyloric valve including a plurality of spaced portions that chyme may pass through and/or around as the chyme enters from the stomach and through and/or around the pyloric valve.

A first side surface 124 of a flange 120 is preferably 1-2 mm apart from a second side surface 126 of an adjacent flange 120 as shown in FIG. 5. First blocking member or inlet 102 defines at least one entryway 128 formed by the separation in a first side surface 124 of a flange 120 and a second side surface 126 of an adjacent flange 120. Entryways 128 are adapted to receive chyme therethrough in order for the chyme to move distally on to flanges 120 of additional blocking members 138 that are located distally along pyloric valve 100 or rather move distally to phalanges 114 or sleeve 110. While entryways 128 preferably have a width of 1-2 mm, it is contemplated by the present invention that entryways may have a width of 0.5-10 mm, or even less than 0.5 mm or even greater than 10 mm.

In the present invention, entryways 128 are preferably configured to receive chyme therethrough. Chyme generally flows from the proximal to distal direction of pyloric valve 100 through entryways 128 and then through pyloric columns 114 and sleeve 110. Chyme generally will contact a proximal surface 122 of a flange 120 before passing through and/or around entryways 128. This is because there is so much more surface area on proximal surfaces 122 for the chyme to contact than entryways 128 to pass through and/or around. Some chyme may pass through entryways 128 of inlet 102 without having contacted proximal surface 122 of flanges 120. In such instances, chyme passes around flanges 120 between flanges 120 and surround skin tissue.

Prior to the chyme contacting the first blocking member or inlet 102 of valve 100, the consistency of the chyme generally allows for some of the chyme to build-up proximally of the proximal surfaces 122 of flanges 120 such that satiety receptors 80 may become activated. The function of flanges 120 of inlet 102 is to inhibit the flow of chyme through and/or around inlet 102 such that chyme may preferably pass only through and/or around entryways 128 of inlet 102.

After chyme passes through and/or around entryways 128 of inlet 102, the chyme preferably flows towards blocking members 112 of valve 100. Blocking members 112 are configured to preferably rest against inner surface 32 of stomach tissue in pyloric antrum 60 proximally to pyloric sphincter 20. Blocking members 112 are preferably a plurality of evenly spaced rows 138. Each row 138 of blocking members 112 is structured much like first blocking member or inlet 102. Blocking members 112 may be located along the length of valve 100 between inlet 102 and pyloric columns 114 in a staggered manner. Each row 138 may include four flanges 140, but each row 138 preferably includes at least one flange 140. In an embodiment wherein a row 138 includes only one flange 140 there is no entryway in row 138. Each flange 140 preferably has a proximal surface 142 adapted to receive chyme thereon. Each flange 140 preferably further includes a first side surface 144 and a second side surface 146 representing the thickness of each flange 140. A first side surface 144 of a flange 140 is preferably 1-2 mm apart from a second side surface 146 of an adjacent flange 140 as shown generally in FIG. 5.

Each row 138 further includes at least one entryway 148 formed by the separation in a first side surface 144 of a flange 140 and a second side surface 146 of an adjacent flange 140, entryway 148 adapted to receive chyme therein such that chyme passes onto another flange 140 located distal to entryway 148 or rather travels distally to pyloric columns 114. While entryways 148 preferably have a width of 1-2 mm, it is contemplated by the present invention that entryways may have a width of 0.5-10 mm, or even less than 0.5 mm or even greater than 10 mm.

Entryways 148 are configured to receive chyme therethrough. Chyme generally will contact a proximal surface 142 of a flange 140 of a row 138 before passing through an entryway 148 or rather between a flange 140 and surrounding skin tissue. Chyme may therefore contact a proximal surface 142 of a flange 140 and then flow through an entryways 148 of a row 138 and onto a subsequent row 138 located distal to the row 138 the chyme flowed from.

As stated above, there are preferably four rows 138 of blocking members 112. Each row 138 may include four flanges 140 of which each flange includes a median portion 150, wherein each median portion 150 of each flange 140 of a respective row 138 is located 90° in a circumferential direction from an adjacent median portion 150. Located distally from a first row 138 is a second row 138 of flanges 140, wherein the flanges 140 of the second row 138 are preferably located 45° in a circumferential direction from the median portion 150 of the flanges 140 of the first row 138. Located distally from the second row 138 is a third row 138 of flanges 140, wherein the flanges 140 of the third row 138 are preferably located 45° in a circumferential direction from the median portion 150 of the flanges 140 of the second row 138. Therefore, as chyme passes through an entryway 128 or 148, the chyme will generally hit a flange 140 of a distally located row 138 before flowing through an entryway 148 of the distally located row 138 or between a flange 140 of the row 138 and the skin tissue surrounding the flange 140.

The chyme may then continue to move in a distal direction through valve 100 wherein the chyme will flow off of a flange 140 of a row 138 and onto a flange 140 of a subsequent row 138 impeding the flow of the chyme through blocking members 112 of valve 100. The flanges and entryways of rows are preferably misaligned in the manner described above but may be misaligned in a different manner such that median portions 150 of flanges 140 are located 30° to 60° in a circumferential direction from an adjacent median portion located distally or proximally to it.

Located distal to blocking members 112 are pyloric columns 114. Preferably, valve 100 includes four pyloric columns 114, but it is contemplated by the present invention that valve 100 includes at least two pyloric columns 114. Valve 100 is implanted in the pyloric region such that pyloric columns 114 are located adjacent pyloric sphincter 20. Pyloric columns 114 are preferably compliant and flexible such that the natural peristaltic action of pyloric sphincter is not impeded. Pyloric columns 114 are preferably separated such that chyme passing from blocking members 112 may pass through a separation in pyloric columns 114 and into sleeve 110.

Figure 6:
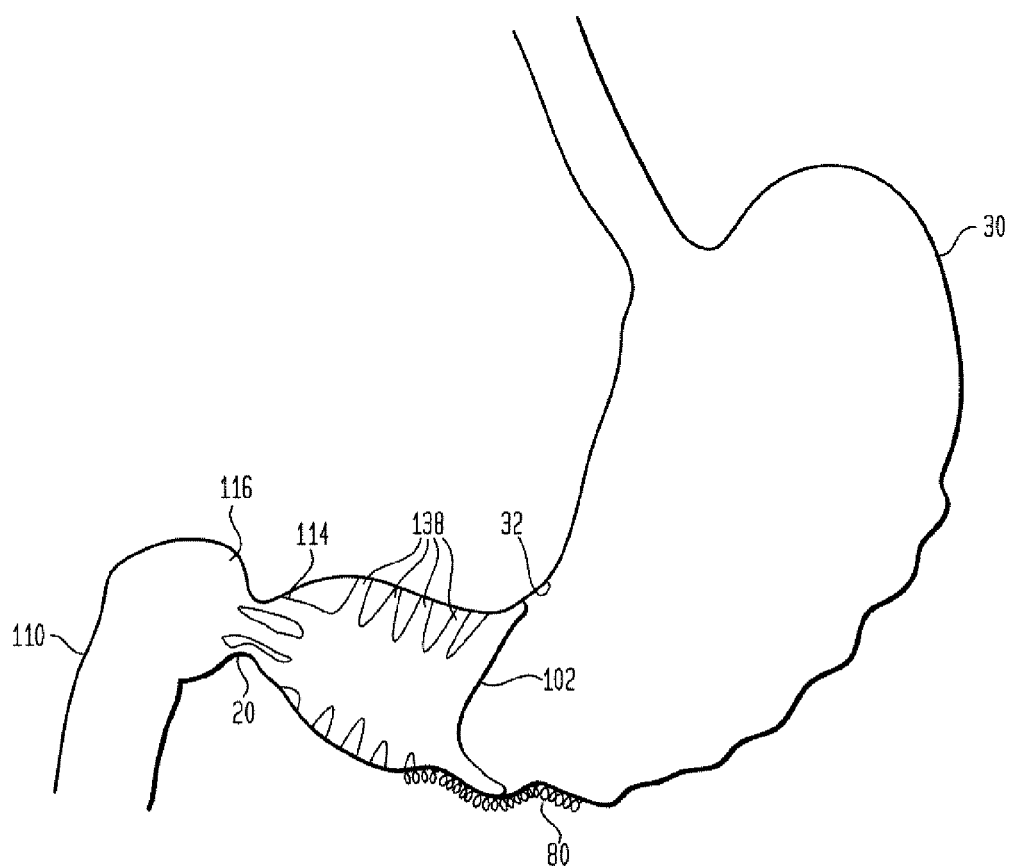
FIG. 6 is a view of the pyloric valve of FIG. 2 implanted along the portion of the gastrointestinal tract shown in FIG. 1.
Figure 7:
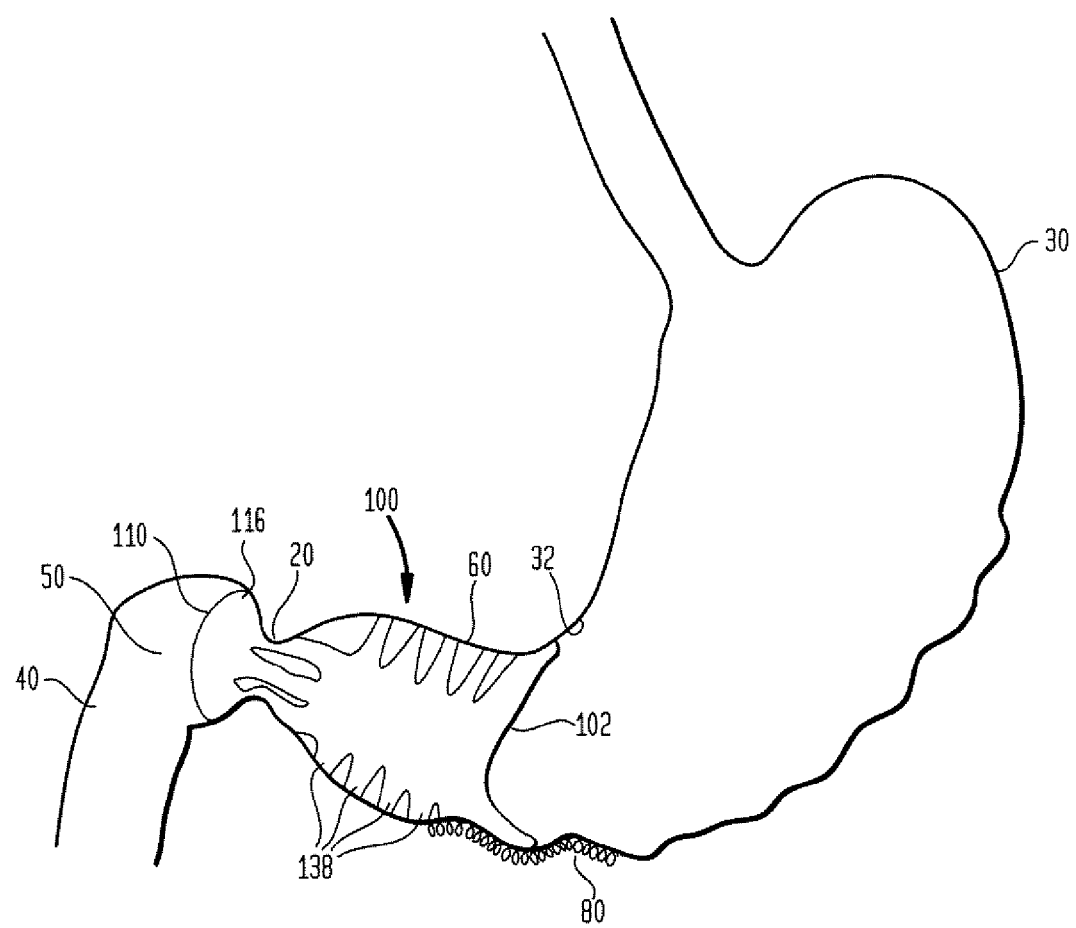
FIG. 7 is a view of another embodiment of a pyloric valve in accordance with the present invention shown implanted along the portion of the gastrointestinal tract shown in FIG. 1.

Valve 100 is implanted in the pyloric region such that sleeve 110 is located just distal to pyloric sphincter 20. Sleeve 110 may have an elongate length such that sleeve 110 passes through duodenum 50 and into small intestines 40 as shown in FIG. 6 or rather may have a terminal portion 108 terminating in duodenum 50 such that it is not located in small intestines 50 as shown in FIG. 7.

As chyme passes through duodenal ring 116 from pyloric columns 114, the chyme preferably flows into sleeve 110 of valve 100. Depending on a particular patient, sleeve 110 of valve 100 may be 0.5 inches to 24 inches long. Preferably, duodenal ring 116 is located near a proximal end of sleeve 110 and preferably acts as a fixation portion for sleeve 110. Duodenal ring 116 generally is configured to help maintain the position of sleeve 110 in a position located just distal to pyloric sphincter 20.

In one embodiment, a fixation portion of sleeve 110 may be a tapered portion that has a slightly greater thickness than the rest of sleeve 110. This greater thickness preferably allows the fixation portion of sleeve 110 to engage surrounding inside tissue of the duodenum or small intestine, thereby inhibiting movement of the fixation portion within the duodenum or small intestine.

A function of sleeve 110 in valve 100 is to aid in inhibiting malabsorption in the duodenum and/or small intestines. As mentioned above, malabsorption is generally known as a state arising from abnormality in digestion or absorption of food nutrients across the gastrointestinal tract. Sleeve 110 acts as a passage for chyme to flow through, wherein when the chyme passes through the sleeve, the chyme may not contact the tissue lining on the inside of the duodenum and/or small intestine and therefore cannot be absorbed into and/or through the lining on the duodenum and/or small intestine.

Preferably, sleeve 110 of valve 100 further includes at least one aperture 180 configured to receive bile secreted from the pancreas therein. Bile of the pancreas generally is used to aid in the digestion process. Therefore, at least one aperture 180 in sleeve 110 allows bile to enter sleeve 110 and aid in digesting the chyme flowing through sleeve 110.

The distal or terminal portion 108 of sleeve 110 may include a radiopaque marker 190 therein. The radiopaque marker 190 may be a nitinol insert that functions to show up on an X-ray so that a surgeon may locate the distal end 106 of valve 100 within gastrointestinal track 10. Radiopaque marker 190 may alternatively be a bead located within sleeve 110 or on outside surface 111 of sleeve 110. Alternatively, a radiopaque silicone-barium mixture may be used to manufacture the device. Preferably, sleeve 110 has a constant diameter throughout its length.

In another embodiment, an inlet 202 of a valve 200 is configured to receive chyme therein. Inlet 202 preferably includes a compliant circular frame 204 or ring that may be collapsed in order to pass through endoscope 90, wherein compliant ring 204 may thereafter expand to conform to tissue on inside surface 32 of stomach 30. While compliant ring 204 of inlet 202 is configured to engage inside surface 32 of stomach 30, it is not configured to over-distend the stomach wall. Preferably, inlet 202 acts as a funnel to receive chyme therein before passing through to phalanges 222 of valve 200. Inlet 202 preferably includes a plurality of entryways 228 therein which serve to allow chyme to pass therethrough but also includes a plurality of spaced apart flanges 220 which form entryways 228 that serve to inhibit the rate of passage of chyme therethrough and/or around.

As chyme passes through and/or around entryways 228 in inlet 202, the chyme will contact a staggered flange 240 of phalanges 222. Preferably, phalanges 222 include a plurality of rows 238 of staggered flanges 240.

FIG. 8 shows another embodiment of a pyloric valve in accordance with the present invention. Pyloric valve 300 includes a duodenal ring 316 having a larger circumference. Duodenal ring 316 is preferably configured to aid in anchoring pyloric valve 300 in the pyloric region while still allowing the natural peristaltic action of the pyloric sphincter to occur. As described above, after pyloric valve 300 is implanted in the pyloric region, duodenal ring 316 is preferably located distal to the pyloric sphincter in the duodenum. Preferably, the circumference of duodenal ring 316 closely matches that of the surrounding tissue. It should be understood that duodenal ring 316 may have a diameter that is slightly larger than the surrounding tissue such that the surrounding tissue may slightly stretch while duodenal ring 316 is anchored in the duodenum.

Preferably, sleeve 310 may include a plurality of slits 320 therethrough configured to receive bile secreted from the pancreas therein. Therefore, at least one slit 320 in sleeve 310 allows bile to enter sleeve 310 and aid in digesting the chyme flowing through sleeve 310.

In FIG. 9, pyloric valve 300' includes a shorter sleeve 310'. Sleeve 310' may still be positioned inside the small intestines after pyloric valve 300' is implanted in the pyloric region. As described above, a function of sleeve 310' is to aid in inhibiting malabsorption in the duodenum and/or small intestines. Preferably, sleeve 310' acts as a passage for chyme to flow through. Here, sleeve 310' is shorter, and chyme will come in contact with tissue of the small intestine faster than it would if pyloric valve 300 having a longer sleeve 310 was instead implanted in the pyloric region.

FIG. 10 shows another embodiment of a pyloric valve in accordance with the present invention. Pyloric valve 400 has no entryways in inlet 402 or blocking members 412. In this embodiment, all the chyme passing through pyloric valve 400 will have to pass around inlet 402 and blocking members 412 between the perimeter of inlet 402 and blocking members 412 and the surrounding tissue. The chyme that passes around inlet 402 and blocking members 412 will eventually travel around and/or through the pyloric columns 414, duodenal ring 416 and sleeve 410 of pyloric valve 400.

In FIG. 11, pyloric valve 400' includes a shorter sleeve 410'. Sleeve 410' may still be positioned inside the small intestines after pyloric valve 400' is implanted in the pyloric region. As described above, a function of sleeve 410' is to aid in inhibiting malabsorption in the duodenum and/or small intestines. Preferably, sleeve 410' acts as a passage for chyme to flow through. Here, sleeve 410' is shorter, and chyme will come in contact with tissue of the small intestine faster than it would if pyloric valve 400 having a longer sleeve 410 was instead implanted in the pyloric region.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pyloric valve comprising:
    an internal tubular structure;
    a plurality of axially connected blocking members located along a longitudinal axis of the valve in a proximal to distal direction and extending radially outward from the internal tubular structure,
    wherein each blocking member defines at least one entryway adapted to receive chyme therethrough,
  wherein the at least one entryway defined by each blocking member is not aligned along the longitudinal axis with the at least one entryway defined by each blocking member adjacent thereto.

2. The pyloric valve of claim 1, wherein the plurality of axially connected blocking members each includes a first side surface, a second side surface, and a proximal surface, wherein the proximal surface is adapted to receive the chyme thereon.

3. A pyloric valve comprising:
    a proximal section including an internal tubular structure and a plurality of axially connected blocking members located along a longitudinal axis of the valve in a proximal to distal direction and extending radially outward from the internal tubular structure, each blocking member defining at least one entryway adapted to receive chyme therethrough;
    wherein the at least one entryway defined by a first blocking member is not aligned with the at least one entryway defined by a second blocking member located adjacent to the first blocking member in the distal direction along the longitudinal axis such that chyme passing through the at least one entryway defined by the first blocking member cannot travel in a linear path through the at least one entryway defined by the second blocking member; and
    a distal section connected to the proximal section distally along the longitudinal axis, the distal section including an elongate sleeve adapted for the passage of the chyme therein.

4. The pyloric valve of claim 3, wherein each of the plurality of blocking members includes at least one blocking portion having a first side surface, a second side surface, and a proximal surface, wherein the proximal surface is adapted to receive chyme thereon.

5. The pyloric valve of claim 4, wherein the at least one entryways are formed between the first side surface and the second side surface of the at least one blocking portion.

6. The pyloric valve of claim 4, wherein an at least one entryway is formed between adjacent first and second side surfaces of adjacent blocking portions.

7. The pyloric valve of claim 6, wherein the at least one entryway is approximately 1-2 mm in width.

8. The pyloric valve of claim 3, further comprising an intermediate section having a plurality of spaced columns connecting the proximal section to the distal section.

9. The pyloric valve of claim 3, wherein the elongate sleeve includes at least one aperture therethrough, the at least one aperture adapted to receive fluid such as bile or other gastric secretions therein.

10. The pyloric valve of claim 3, wherein the sleeve includes a radiopaque marker located on a surface of the sleeve.

11. A method of regulating the flow of chyme through a stomach of a patient, comprising:

implanting a pyloric valve into the pyloric region between a stomach and small intestines of the patient, the pyloric valve comprising:
    an internal tubular structure;
    an inlet formed at a proximal end of the pyloric valve, the inlet having at least one entryway adapted to receive chyme therethrough; and
    at least one blocking member located distal to the at least one entryway of the inlet and extending radially outward form the internal tubular structure, the blocking member adapted to receive chyme having flowed through the at least one entryway of the inlet thereon, the at least one blocking member having at least one entryway not aligned with the at least one entryway of the inlet, wherein the chyme passing through the at least one entryway of the inlet cannot travel in a linear path through the at least one entryway of the blocking member.

12. The method of claim 11, wherein the pyloric valve further comprises an elongate sleeve located distal to the at least one blocking member, the elongate sleeve adapted for the passage of chyme therein.

* * * * *